United States Patent
Rhee et al.

(10) Patent No.: US 8,128,794 B2
(45) Date of Patent: Mar. 6, 2012

(54) WATER POLLUTION SENSOR FOR DETECTING HEAVY METAL AND METHOD OF MANUFACTURING THE SAME

(75) Inventors: Chang Kyu Rhee, Daejeon (KR); Gyoung-Ja Lee, Daejeon (KR); Hi Min Lee, Seoul (KR); Min Ku Lee, Daejeon (KR); Sang-Hoon Lee, Daejeon (KR); Sung Mo Hong, Daejeon (KR); Jong Keuk Lee, Ulsan (KR); Ju Myoung Kim, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 396 days.

(21) Appl. No.: 12/121,016

(22) Filed: May 15, 2008

(65) Prior Publication Data

US 2008/0283395 A1 Nov. 20, 2008

(30) Foreign Application Priority Data

May 16, 2007 (KR) .................. 10-2007-0047700
Feb. 15, 2008 (KR) .................. 10-2008-0014011

(51) Int. Cl.
*G01N 27/26* (2006.01)

(52) U.S. Cl. ........ 204/400; 204/401; 204/431; 204/432; 205/790; 205/794.5

(58) Field of Classification Search .......... 204/400–432; 205/790, 794.5

See application file for complete search history.

(56) References Cited

U.S. PATENT DOCUMENTS

| | | | |
|---|---|---|---|
| 6,682,647 B1 * | 1/2004 | Wang ........................ | 205/775 |
| 7,132,188 B2 * | 11/2006 | Masel et al. ................ | 429/494 |
| 2004/0004209 A1 * | 1/2004 | Matsuba et al. ........... | 252/518.1 |
| 2004/0256228 A1 * | 12/2004 | Huang ........................ | 204/434 |
| 2007/0235330 A1 * | 10/2007 | Lyuu ........................ | 204/403.01 |

FOREIGN PATENT DOCUMENTS

| | | |
|---|---|---|
| KR | 1020020007800 A | 1/2002 |
| KR | 1020050056288 A | 6/2005 |
| KR | 1020060104939 A | 10/2006 |

* cited by examiner

*Primary Examiner* — Keith Hendricks
*Assistant Examiner* — Bach Dinh
(74) *Attorney, Agent, or Firm* — Hammer & Associates, P.C.

(57) ABSTRACT

A water pollution sensor for detecting a heavy metal, the water pollution sensor including: a base member; a conductive layer formed at a portion of one of surfaces of the base member and consisting of a conductive material; an insulating layer formed on the conductive layer to enable a portion of the conductive layer to be exposed; and a bismuth layer formed on a portion of the exposed conductive layer and including bismuth powders.

8 Claims, 4 Drawing Sheets

WATER POLLUTION SENSOR FOR DETECTING HEAVY METAL AND METHOD OF MANUFACTURING THE SAME

CROSS-REFERENCE TO RELATED APPLICATION

This application claims the benefit under 35 U.S.C. §119(a) of Korean Patent Application No. 10-2007-0047700, filed on May 16, 2007, and Korean Patent Application No. 10-2008-0014011, filed on Feb. 15, 2008 in the Korean Intellectual Property Office, the entire disclosures of which are hereby incorporated by reference.

BACKGROUND OF THE INVENTION

1. Field of the Invention

The present invention relates to a water pollution sensor for detecting a heavy metal and a method of manufacturing the same, and more particularly, to a water pollution sensor for detecting a heavy metal and a method of manufacturing the same which is reliable, environmentally-friendly, and competitive in manufacturing.

2. Description of Related Art

In general, a stripping voltammetry, one type of electroanalysis, concentrates heavy metals in water on an electrode surface using a property of Oxidation Reduction Potential (ORP) of each heavy metal, releases the heavy metals into the water again, and analyzes a particular current change, that is, voltammogram generated when releasing, for quantitative analysis of heavy metals in a solution.

In a stripping voltammetry, since a reactant is concentrated on an electrode surface in advance, sensitivity considerably increases, and thus the extremely small amount of each compound may be determined. Also, since an electrolytic concentration process is performed in a particular electric potential, the selection of analysis may increase. Currently, a hanging mercury drop electrode mainly using mercury and a mercury thin film electrode are mainly used as a working electrode for s stripping voltammetry. An environmentally-friendly, non-toxic, mercury-free replacement electrode has been developed due to a mercury disposal issue, a surface process issue for reproducibility of an analysis result, a change in the air, and the like.

Currently, much research on a thin bismuth layer electrode including a glassy carbon electrode as a base substrate so as to replace electrode material for a stripping voltammetry has been conducted. However, when using a bismuth layer, several steps of surface cleansing and processing procedures at every measurement are required for sensitivity and reproducibility of analysis results. The surface processing significantly affects restoration and functionality of a working electrode, which is associated with accuracy and reliability of analysis results. Also, the surface processing may limit online measurement analysis in an automatic system and limit the use for a portable measurement device.

BRIEF SUMMARY

An aspect of the present invention provides a water pollution sensor for detecting a heavy metal which is environmentally-friendly, simply manufactured, disposable, and inexpensive when a stripping voltammetry is applied.

Another aspect of the present invention also provides a method of manufacturing a water pollution sensor for detecting a heavy metal which may efficiently manufacture the water pollution sensor for detecting a heavy metal.

According to an aspect of the present invention, there is provided a water pollution sensor for detecting a heavy metal, the water pollution sensor including: a base member; a conductive layer formed at a portion of one of surfaces of the base member and consisting of a conductive material; an insulating layer formed on the conductive layer to enable a portion of the conductive layer to be exposed; and a bismuth layer formed on a portion of the exposed conductive layer and including bismuth particles.

In an aspect of the present invention, the conductive material may be a conductive carbon ink.

In an aspect of the present invention, the base member may have a bar shape, and the conductive layer may be formed on a side of the base member to be parallel to a longitudinal line of the base member and has a stripe shape.

In an aspect of the present invention, the insulating layer may be formed on the conductive layer to enable both ends of the conductive layer to be exposed.

In an aspect of the present invention, the bismuth layer may be formed on either end of the both ends of the conductive layer.

In an aspect of the present invention, the conductive layer may have a thickness of about 20 μm to about 100 μm, and the bismuth layer may include the bismuth particles of about 2 μg to about 5 μg per unit area of 1 $cm^2$.

In an aspect of the present invention, the bismuth layer may include a bismuth particles having a size of about 6 nm to about 300 μm, and the bismuth layer may further include a polymer binder with a permeability of ion.

According to another aspect of the present invention, there is provided a method of manufacturing a water pollution sensor for detecting a heavy metal, the method including: printing a conductive material on a portion of one of surfaces of a base member to form a conductive layer; printing an insulating material on the base member to enable a portion of the conductive layer to be exposed to form an insulating layer; dispersing bismuth powders in a spreading solvent to prepare bismuth dispersion; and dropping the bismuth dispersion on a portion of the exposed conductive layer to be dried.

In an aspect of the present invention, the spreading solvent may be a polymer binder aqueous solution with a concentration of about 0.1% to 10%, or distilled water, and the polymer binder aqueous solution has a permeability of ion.

In an aspect of the present invention, the bismuth powders may be manufactured by a gas condensation method.

Additional aspects, features, and/or advantages of the invention will be set forth in part in the description which follows and, in part, will be apparent from the description, or may be learned by practice of the invention.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION OF EMBODIMENTS

Figure 1:
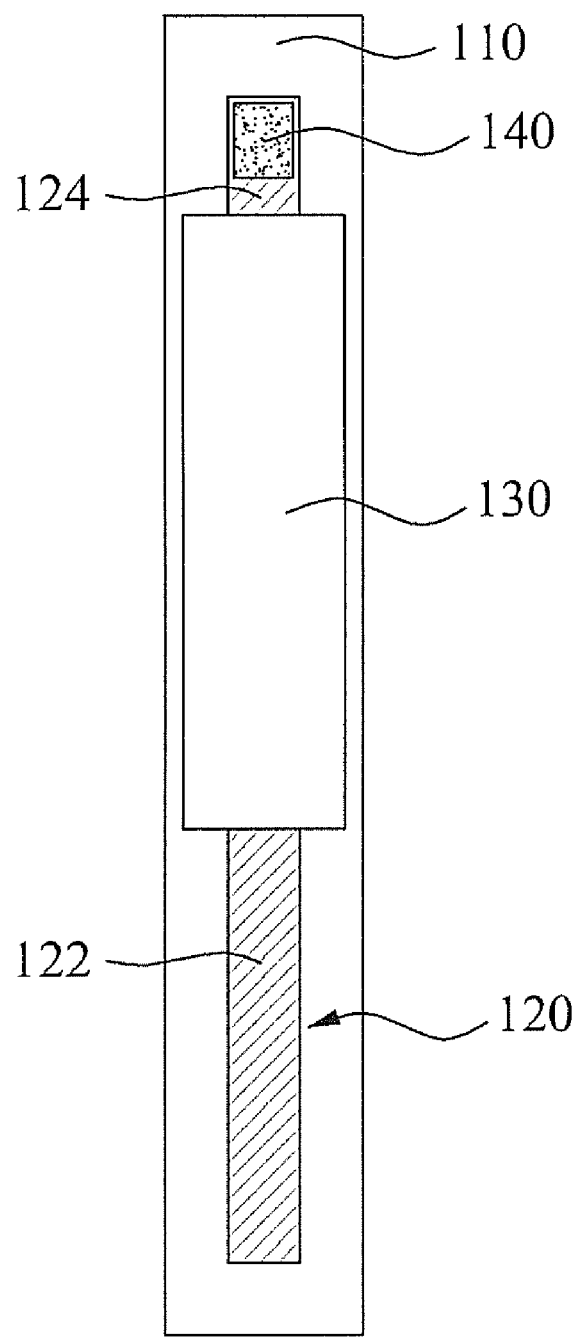
FIG. 1 is a top view illustrating a water pollution sensor for detecting a heavy metal according to an embodiment of the present invention.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

FIG. 1 is a top view illustrating a water pollution sensor 100 for detecting a heavy metal according to an embodiment of the present invention.

Referring to FIG. 1, the water pollution sensor 100 for detecting a heavy metal includes a base member 110, conductive layer 120, insulating layer 130, and bismuth layer 140.

A variety of materials having a smooth surface and strong adhesive strength may be used as the base member 110. In the present embodiment, a polymer film may be used as the base member 110. A type of polymer film is not limited.

Also, in the present embodiment, the base member 110 is a bar-shaped thin film. However, a shape of the base member 110 is not limited.

For example, the conductive layer 120 may be formed by screen printing a conductive carbon ink on a portion of one of surfaces of the base member 110. The conductive carbon ink, conductive polymer, and the like may be used as a material for the conductive layer 120. It is preferable that carbon is included in the conductive material.

The conductive carbon ink is dried in a predetermined temperature after the screen printing, and thus the conductive layer 120 is formed.

The conductive layer 120 has a stripe shape to be parallel to a longitudinal line of the base member.

A thickness of the conductive layer 120 may affect a reliability of the water pollution sensor 100 for detecting a heavy metal. When the conductive layer 120 is extremely thin, electrical disconnection may occur. It is preferable that the thickness of the conductive layer 120 is about 20 μm to about 100 μm, specifically, around 80 μm.

The insulating layer 130 may be formed by screen printing an insulating ink on the conductive layer 120. As described above, the insulating ink is required to be dried at a predetermined temperature after the screen printing to form the insulating layer 130.

The insulating layer 130 may be formed on the conductive layer 120 to enable a portion of the conductive layer 120 to be exposed. Referring to FIG. 1, the insulating layer 130 may be formed on a middle part of the conductive layer 120, and thus a first conductive layer area 122 and second conductive layer area 124 are exposed.

In FIG. 1, the first conductive layer area 122 may be relatively longer than the second conductive layer area 124. The first conductive layer area 122 may function as a connection portion to be applied with external electricity. The bismuth layer 140 may be formed on a portion of the second conductive layer area 124.

The bismuth layer 140 may be formed on a portion of the exposed conductive layer 120, that is, the portion of the second conductive layer area 124.

The bismuth layer 140 may be formed by dropping a bismuth dispersion on the second conductive layer area 124 and drying.

The bismuth dispersion may be obtained by evenly dispersing bismuth powders in a spreading solvent. The bismuth powders may be manufactured by a gas condensation method for an efficient removal of impurities.

When the bismuth powders includes a bismuth particles having a size greater than about 300 nm, a performance of the water pollution sensor 100 for detecting a heavy metal may significantly deteriorate. Accordingly, the bismuth powders may include bismuth particles having a size of less than about 300 nm, and preferably may include particles having a size of about 6 nm to about 75 nm.

Ethanol, distilled water, and the like may be used as the spreading solvent to prepare the bismuth dispersion. Also, it is preferable that the spreading solvent may be a polymer binder aqueous solution with a concentration of about 0.1% to 10%, and the polymer binder aqueous solution may have a permeability of ion.

The polymer binder with the permeability of ion may be Nafion™. Also, any resin with the permeability of ion, which has a high conductivity of hydrogen ion and high chemical/physical strength, may be used.

Nafion™ is a product name of a polymer electrolyte developed by DuPont. In Nafion™, sulfonic acid radical is adhered to chanin of Teflon ($—CF_2\text{-}CF_2—$) polymer. The chain consists of perfluororadical. Also, Nafion™ has a superior hydrogen ion conductivity (0.08 S/cm at 30° C.) and superior chemical and physical strength.

It is preferable that the bismuth layer 140 may include the bismuth powders of about 2 μg to about 5 μg per unit area of 1 $cm^2$.

Hereinafter, a result of measuring a sensor sensitivity performed to evaluate a performance of the water pollution sensor 100 for detecting a heavy metal according to an embodiment of the present invention is described in detail. However, the present invention is not limited to the described exemplary embodiments.

[Experiment]

1. Experiment Target

To manufacture a water pollution sensor for detecting a heavy metal used for the experiment, a bismuth powder aqueous solution of 0.02 g/L is prepared by dispersing bismuth powders in distilled water, and bismuth powder aqueous solution of 10 μl is dropped on a portion of a conductive layer, dried, and fixed. An area of the conductive layer marked by bismuth was 02 □ 0.5 $cm^2$. In this instance, a range of sizes of the bismuth particles is about 6 nm to about 75 nm, and the distilled water includes Nafion of 0.24%.

2. Experiment Method

Ag/AgCl (3 M KCl) is used as a reference electrode. A voltage of −1.4 V is applied for 120 seconds in a solution including 0.1 M acetic-chloride buffer (pH 4.7), and Zinc (Zn), Cadmium (Cd), and Plumbum (PB) ions of 20 ppb, for electrodeposition of above-described ion. Also, as a voltage linearly increases at a speed of 1.0 V/s, a stripping voltammetry is used.

Sensor Sensitivity Depending on a Thickness of a Conductive Layer

To obtain a performance in analytical chemistry depending on a thickness of a conductive layer of a water pollution sensor for detecting a heavy metal according to an embodiment of the present invention, a stripping voltammetry is performed with respect to Zn, Cd, and Pb ions. In this instance, bismuth powders are formed on the water pollution sensor for detecting a heavy metal, and the Zn, Cd, and Pb ions may be simultaneously analyzed.

Table 1 shows a stripping oxidation current value (I) and a test result of reproducibility (R) of an initial oxidation current value after measuring the stripping oxidation current value (I) five times. The stripping oxidation current value (I) is measured using sensors having different conductive layer thicknesses.

TABLE 1

| Thickness of conductive layer | Zn | | Cd | | Pb | |
|---|---|---|---|---|---|---|
| (µm) | R (%) | I (µA) | R (%) | I (µA) | R (%) | I (µA) |
| 40 | 127 | 12.2 | 80 | 11.2 | 81 | 6.9 |
| 80 | 97 | 9.8 | 103 | 10.5 | 99 | 5.9 |

As shown in Table 1, when the thickness of the conductive layer is 40 µm, a higher current value is obtained with respect to each metal ion. However, when the thickness of the conductive layer is 80 µm, a more accurate value with respect to the test result of the reproducibility is obtained.

Accordingly, a stripping voltammetry is performed with respect to the conductive layer having the thickness of 80 µm in experiments below.

Sensor Sensitivity Depending on a Bismuth Content

When manufacturing the water pollution sensor for detecting a heavy metal, to determine an appropriate amount of bismuth powders to be formed on the conductive layer, while an amount of bismuth powders is varied, five types of sensors are manufactured and a stripping voltammetry is performed with respect to Zn, Cd, and Pb ions. A range of sizes of the bismuth particles is about 6 nm to about 75 nm.

Figure 2:
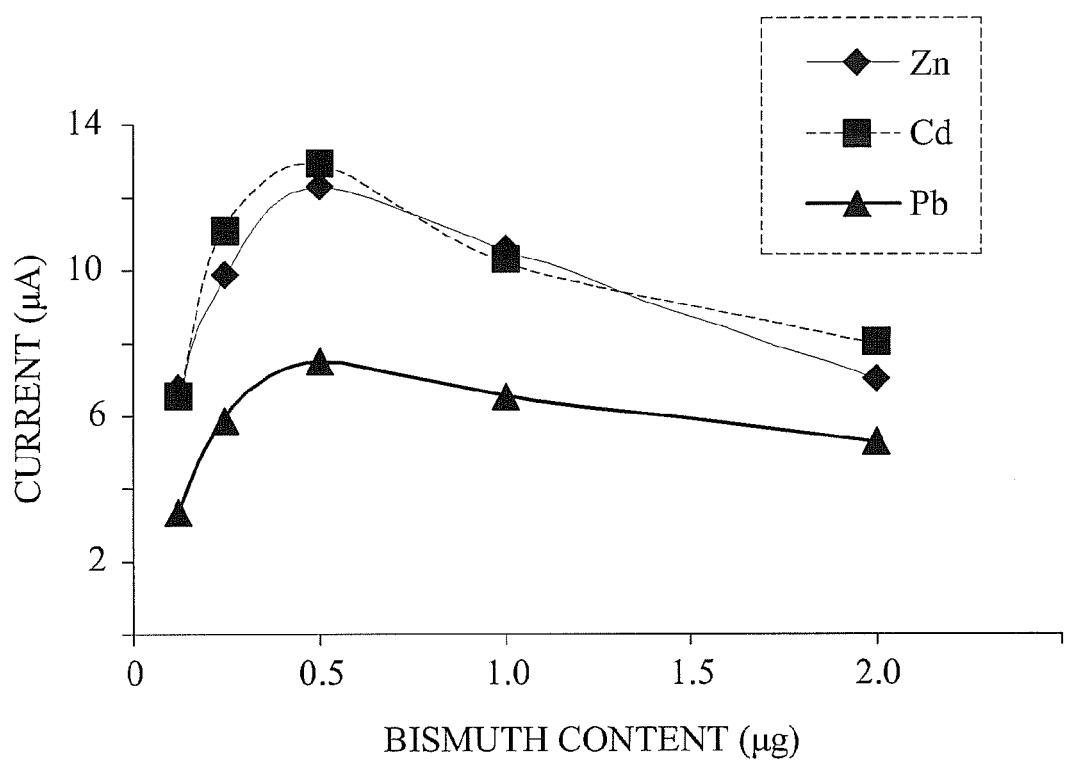
FIG. 2 is a graph illustrating a result of oxidation stripping voltammetry depending on a content of bismuth powders.

FIG. 2 is a graph illustrating a result of oxidation stripping voltammetry depending on a weight of bismuth powders.

Referring to FIG. 2, when the weight of bismuth powders with respect to all the metal ions is 0.125 µg, a lowest stripping voltammetry value is shown. As the weight of bismuth powders increases, a current value gradually increases. When the weight of bismuth powders is 0.5 µg, the current value is maximized, and when the weight of bismuth powders is greater than 0.5 µg, the current value decreases.

Table 2 shows a test result of reproducibility of an oxidation current value of a sensor depending on a weight of the formed bismuth powders.

TABLE 2

| Bi weight | R (%) | | |
|---|---|---|---|
| (µg) | Zn | Cd | Pb |
| 0.125 | 162 | 42 | 65 |
| 0.2 | 97 | 103 | 98 |
| 0.5 | 105 | 99 | 110 |
| 1.0 | 88 | 120 | 116 |
| 2.0 | 58 | 96 | 97 |

As shown in Table 2, a reproducibility with respect to an oxidation current value when the weight of bismuth powders is about 0.2 µg to about 0.5 µg is superior, even after measuring five times. However, the reproducibility is significantly different from an initial value in a sensor having a bismuth powder weight less than about 0.2 µg and a sensor having a bismuth powder weight greater than about 0.5 µg.

Accordingly, an optimum sensor sensitivity is observed when a bismuth powder weight of about 0.2 µg to about 0.5 µg is formed on the conductive layer.

Sensor Sensitivity Depending on a Range of Sizes of Bismuth Powders

When manufacturing a water pollution sensor for detecting a heavy metal, to obtain a performance in an analytical chemistry depending on a range of sizes of bismuth powders, bismuth powder groups having a different range of sizes of bismuth particles are formed and a stripping voltammetry is performed with respect to Zn, Cd, and Pb ions.

A bismuth powder aqueous solution of 0.02 g/L is prepared by dispersing the bismuth powder groups having the different range of sizes of bismuth particles in distilled water. Also, the bismuth powder aqueous solution of 10 µl is dropped on a surface of a conductive layer, and thus a working electrode is prepared.

Figure 3:
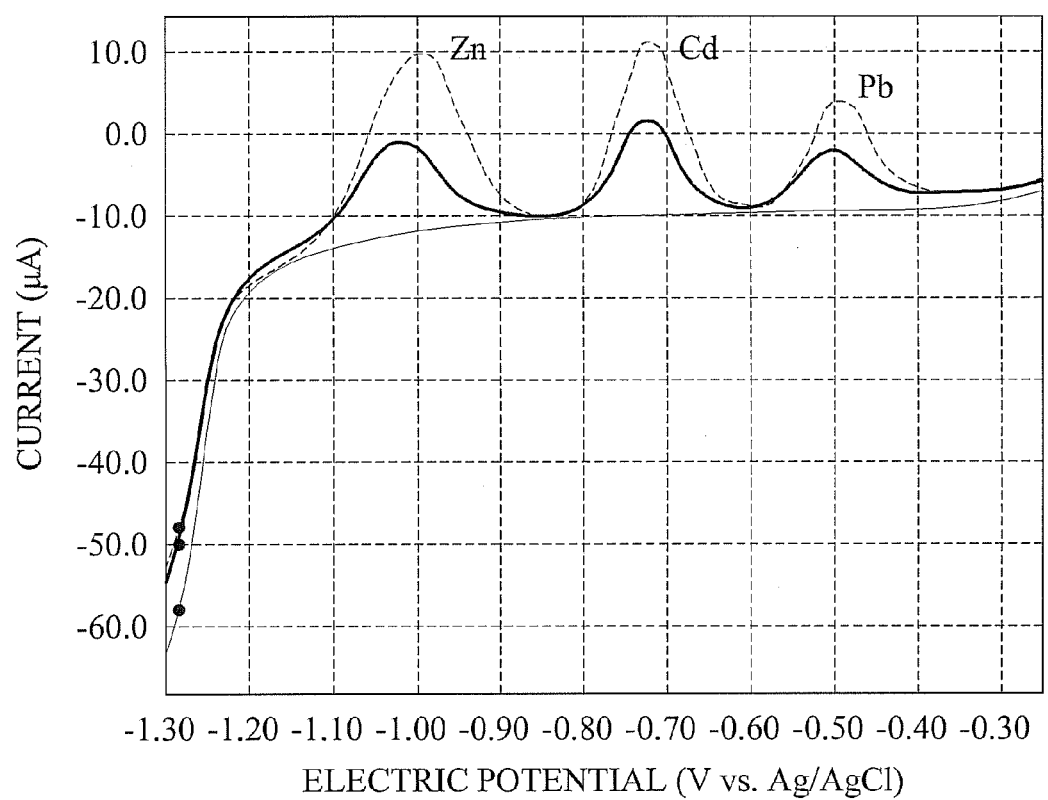
FIG. 3 is a graph illustrating an analysis result obtained by a linear sweep voltammetry while increasing a concentration of each metal ion to 0, 20, and 40 ppb using a sensor where bismuth particles having a size of about 6 nm to about 75 nm are formed.
Figure 4:
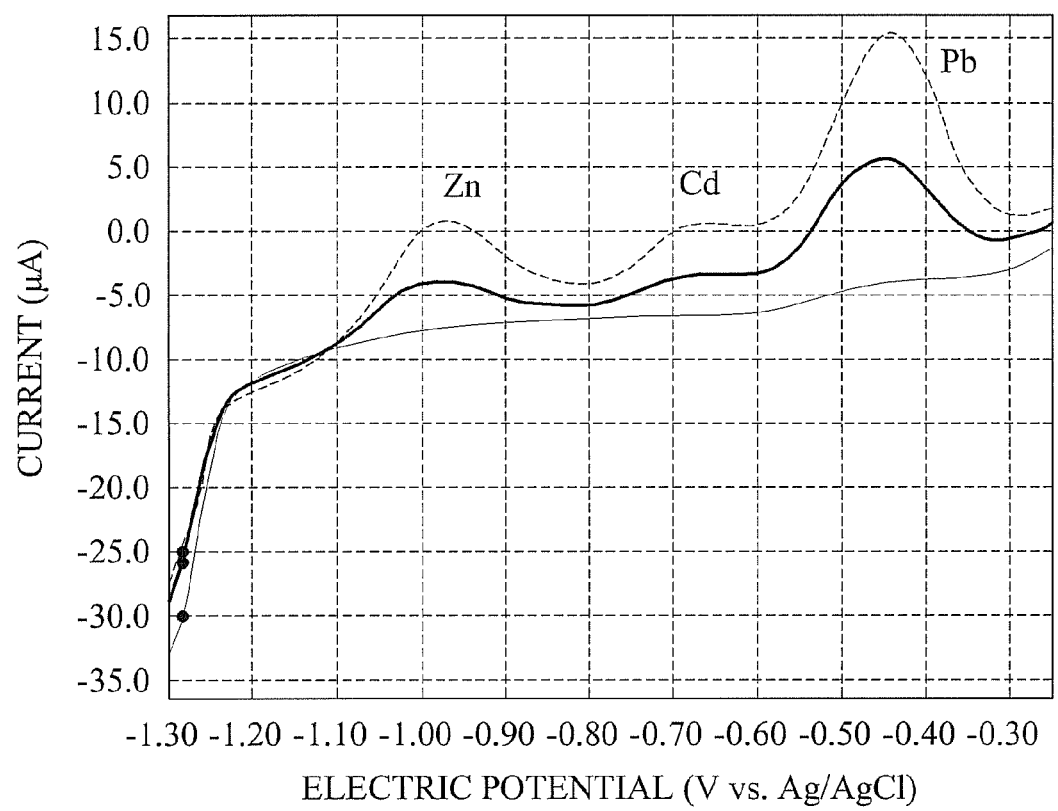
FIG. 4 is a graph illustrating an analysis result of a linear sweep voltammetry while increasing a concentration of each metal ion to 0, 20, and 40 ppb using a sensor where bismuth particles having a size of at least 300 nm are formed.

FIG. 3 is a graph illustrating an analysis result obtained by a linear sweep voltammetry while increasing a concentration of each metal ion to 0, 20, and 40 ppb using a sensor where bismuth powders having a different range of sizes of about 6 nm to about 75 nm are formed. FIG. 4 is a graph illustrating an analysis result of a linear sweep voltammetry while increasing a concentration of each metal ion to 0, 20, and 40 ppb using a sensor where bismuth powders having a wide distribution greater than 300 nm are formed.

As illustrated in FIG. 3, when increasing a concentration of each metal ion by 20 ppb, an oxidation peak current with respect to all the metal ions proportionally increases. Also, a well-defined peak-shaped voltammogram is shown in the graph. However, as illustrated in FIG. 4, a proportionality of peak current is low due to a band spreading.

Table 3 shows a stripping oxidation current value (I) and a test result of reproducibility (R) measured with respect to a solution including Zn, Cd, and Pb ions of 20 ppb using a sensor where bismuth powder groups having a different range of sizes of bismuth particles are formed.

TABLE 3

| Range of sizes of bismuth powders | Zn | | Cd | | Pb | |
|---|---|---|---|---|---|---|
| (nm) | R (%) | I (µA) | R (%) | I (µA) | R (%) | I (µA) |
| 6-75 | 97 | 9.8 | 103 | 10.5 | 99 | 5.9 |
| 6-130 | 103 | 10.6 | 112 | 10.6 | 96 | 5.4 |
| 6-300 | 95 | 9.6 | 103 | 10.0 | 105 | 5.9 |
| Wide distribution | 96 | 4.6 | 62 | 0.9 | 95 | 6.8 |

As shown in Table 3, a reproducibility of an oxidation current value with respect to all the metal ions is relatively accurate when the formed bismuth powders are from about 6 nm to about 75 nm to about 6 nm to 300 nm. However, when having a wide distribution greater than 300 nm, a big difference is shown with respect to Cd ion. Accordingly, the bismuth powder having a size range of at least about 6 nm to about 300 nm is required for a simultaneous analysis.

Sensor Sensitivity Depending on a Spreading Solvent for Forming Bismuth Powders

When manufacturing a water pollution sensor for detecting a heavy metal, to obtain a sensor performance in an analytical chemistry depending on a spreading solvent for forming bismuth powders, bismuth powders are formed on a conductive layer using spreading solvents different from each other and a stripping voltammetry is performed with respect to Zn, Cd, and Pb ions.

A bismuth powder aqueous solution of 0.02 g/L is prepared by dispersing the bismuth powders having a range of sizes of bismuth powders of about 6 nm to about 75 nm in different spreading solvents. Also, the bismuth powder aqueous solution of 10 µl is dropped on a surface of a conductive layer, and thus a sensor is prepared.

Table 4 shows a stripping oxidation current value (I) and a test result of reproducibility (R).

TABLE 4

| Spreading solvent | Zn R (%) | Zn I (µA) | Cd R (%) | Cd I (µA) | Pb R (%) | Pb I (µA) |
|---|---|---|---|---|---|---|
| $H_2O$ | 97 | 9.8 | 103 | 10.5 | 99 | 5.9 |
| $H_2O$ + 0.24% Nafion | 110 | 26.5 | 97 | 25.3 | 105 | 12.5 |
| $H_2O$ + 0.45% Nafion | 110 | 28.8 | 93 | 26.3 | 106 | 15.9 |
| Ethanol | 92 | 7.3 | 40 | 7.8 | 36 | 4.9 |
| Ethanol + 0.24% Nafion | — | — | 63 | 6.1 | 74 | 1.1 |
| Ethanol + 0.45% Nafion | — | — | 75 | 6.6 | 79 | 2.2 |
| Chloroform | 305 | 1.7 | 87 | 7.2 | 78 | 5.5 |

As shown in Table 4, when using ethanol and chloroform as the spreading solvent, the sensor performance in the analytical chemistry is significantly low. However, when using distilled water as the spreading solvent, superior reaction sensitivity is shown.

In particular, when using distilled water where a small amount of polymer binder with a permeability of ion is added as the spreading solvent, a stripping oxidation current value with respect to all the metal ions becomes higher in a polymer binder aqueous solution with a permeability of ion, and sensor sensitivity is improved.

According to the present invention, there is provided a water pollution sensor for detecting a heavy metal which has a superior accuracy and reliability and may be simply manufactured and disposable.

Also, according to the present invention, there is provided a water pollution sensor for detecting a heavy metal which includes harmless bismuth powders, environmentally-friendly, and thereby may replace a mercury electrode in a conventional art.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. Therefore, it is intended that the scope of the invention be defined by the claims appended thereto and their equivalents.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A water pollution sensor for detecting a heavy metal, the water pollution sensor comprising:
   A base member;
   A conductive layer formed on a portion of one of surfaces of the base member and consisting of a conductive material;
   An insulating layer formed on the conductive layer to enable a portion of the conductive layer to be exposed; and
   A bismuth layer formed on a portion of the exposed conductive layer and including bismuth particles having a size in the range of about 6 nm to about 300 nm, and said bismuth layer additionally including a polymer binder with ion permeability,
   Wherein the polymer binder with ion permeability is a sulfonated tetrafluoroethylene.

2. The water pollution sensor of claim 1, wherein the base member is a polymer film.

3. The water pollution sensor of claim 1, wherein the conductive material is a conductive carbon ink.

4. The water pollution sensor of claim 1, wherein the base member has a bar shape, and the conductive layer is formed on a side of the base member to be parallel to a longitudinal line of the base member and has a stripe shape.

5. The water pollution sensor of claim 4, wherein the insulating layer is formed on the conductive layer to enable both ends of the conductive layer to be exposed.

6. The water pollution sensor of claim 5, wherein the bismuth layer is formed on either end of the both ends of the conductive layer.

7. The water pollution sensor of claim 1, wherein the conductive layer has a thickness of about 20 µm to about 100 µm.

8. The water pollution sensor of claim 1, wherein the bismuth layer includes the bismuth particles of about 2 µg to about 5 µg per unit area of 1 $cm^2$.

* * * * *